United States Patent [19]

Wong

[11] Patent Number: 4,900,816

[45] Date of Patent: Feb. 13, 1990

[54] HEMOGLOBIN COMPLEXES

[75] Inventor: Jeffrey T. Wong, Don Mills, Canada

[73] Assignee: Fisons plc, Leicestershire, England

[21] Appl. No.: 197,443

[22] Filed: May 23, 1988

[30] Foreign Application Priority Data

May 23, 1987 [GB] United Kingdom ................. 8712240

[51] Int. Cl.$^4$ ..................... C07H 15/04; C07G 17/00; C08B 37/02; C08B 33/00
[52] U.S. Cl. .................................... 536/120; 530/385; 536/124; 536/112; 536/102; 536/122
[58] Field of Search ............... 536/120, 124, 112, 102, 536/122; 530/385

[56] References Cited

U.S. PATENT DOCUMENTS

| | | | |
|---|---|---|---|
| 4,064,118 | 12/1977 | Wong | 530/385 |
| 4,650,786 | 3/1987 | Wong | 530/385 |
| 4,777,244 | 10/1988 | Bonhard et al. | 530/385 |

Primary Examiner—Ronald W. Griffin
Assistant Examiner—Everett White
Attorney, Agent, or Firm—Marshall, O'Toole, Gerstein, Murray & Bicknell

[57] ABSTRACT

There is described a water soluble compound having a molecular weight of from about 70,000 to about 2,000,000 and having the formula I,

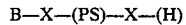

B—X—(PS)—X—(H)   I in which PS is a polysaccharide of molecular weight from about 2,000 to about 2,000,000,
X is a covalently bonded chemical bridging group,
H is a group Hb or Hb—Z
B is a blocked activating group
Hb is a hemoglobin residue, and
Z is an oxygen affinity reducing ligand containing two or more phosphate groups.

There are also described processes for making the compounds, and their formulations and use as oxygen transporting agents.

5 Claims, 1 Drawing Sheet

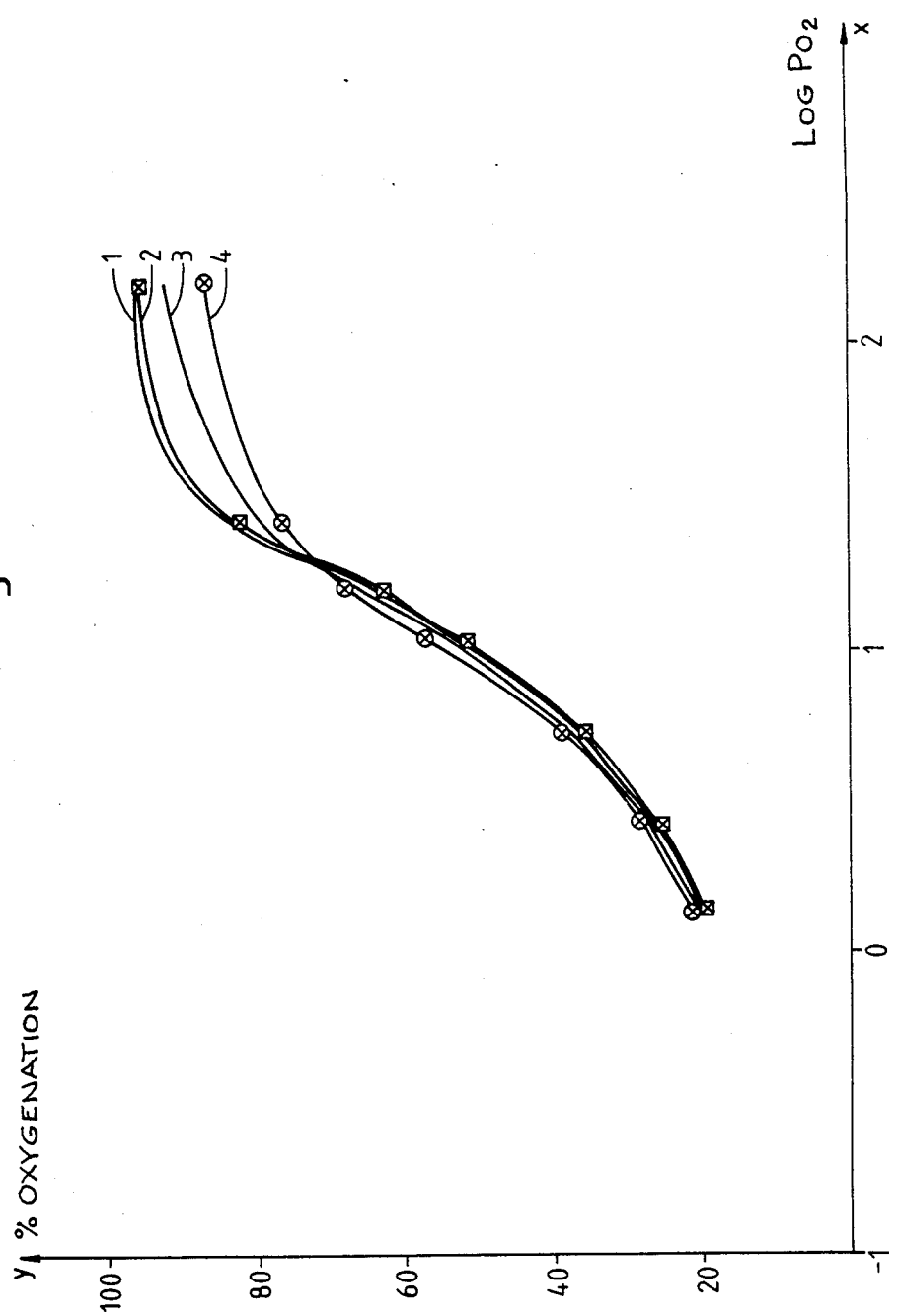

HEMOGLOBIN COMPLEXES

TECHNICAL FIELD

This invention relates to blood substitutes and methods for their preparation.

Pyridoxal-5-phosphate is known to bind to haemoglobin in a reversible manner, and it is also known that this binding can be made irreversibly by reduction, both the reversibly and the irreversibly bound products having less strong oxygen binding characteristics than the haemoglobin itself. However, it has been found that covalent derivatization with pyridoxal-5'-phosphate fails to reduce the oxygen affinity of dextran-haemoglobin to approach that of haemoglobin derivatized with pyridoxal-5'-phosphate (PLP-Hb). An oxygen affinity close to or below that of PLP-Hb is considered desirable for a satisfactory haemoglobin-based blood substitute.

BACKGROUND ART

U.S. Pat. No. 4,064,118 describes a composition useful as a blood substitute or a blood extender which comprises the water soluble product of covalently coupling haemoglobin with dextran having a molecular weight of from about 5,000 to about 2,000,000.

It has however been found that, as compared with haemoglobin, the products according to U.S. Pat. No. 4,064,118 tend to show a somewhat greater affinity for oxygen, but retain the essential oxygen transporting and releasing capability of haemoglobin.

U.S. Pat. No. 4,650,786 describes a modified dextran-haemoglobin complex having reduced oxygen affinity. This modified dextran-haemoglobin complex is prepared by first activating the dextran moeity, and then reacting the activated dextran with haemoglobin or a haemoglobin-inositol tetrakis phosphate dialdehyde (FPA) complex.

However, dextran-haemoglobin complexes and modified dextran-haemoglobin complexes suffer from the disadvantage that the viscosity of an aqueous solution increases on storage, e.g. for 12 days or more, to such an extent so as to render them unsuitable for administration.

We have now surprisingly found that the activated sites on the dextran moiety may be blocked, and the viscosity on storage improved, without affecting the oxygen transport properties of the haemoglobin complex.

SUMMARY OF THE INVENTION

The invention would be understood from the description that follows taken in conjunction with the accompanying drawing in which FIG. 1 shows the oxygen dissociation curve of typical products of the invention.

According to the invention, we provide a water soluble compound having a molecular weight of from about 70,000 to about 2,000,000 and having the formula I,

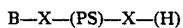

in which PS is a polysaccharide of molecular weight from about 2,000 to about 2,000,000,
X is a covalently bonded chemical bridging group,
H is a group Hb or Hb-Z
B is a blocked activating group
Hb is a haemoglobin residue, and
Z is an oxygen affinity reducing ligand containing two or more phosphate groups.

According to the invention, we also provide a process for the production of a compound of formula I, which comprises reaction of a compound of formula II,

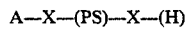

in which X, H, and PS are as defined above, and
A is an activating group,
with a compound capable of blocking an activating group.

The activating group must be capable of reacting with the hydroxyl groups of the polysaccharide. In addition, it must be capable of subsequent reaction with haemoglobin. Among the available groups on haemoglobin are, e.g. amino, phenolic, sulphydryl, thiomethyl, imidazo, carboxyl and guanidine.

Thus the activating group may comprise:

(i) an acrylating group which reacts with an amino group on the haemoglobin molecule;

(ii) an alkylating group which reacts with sulphydryl, thiomethyl, imidazo or amino groups on the haemoglobin molecule;

(iii) an ester or amide forming group which reacts with a carboxyl group on the haemoglobin molecule;

(iv) a disulphide forming group which reacts with the sulphydryl group on the haemoglobin molecule;

(v) a dicarbonyl group which reacts with the guanidono group on the haemoglobin molecule;

(vi) a diazo group which reacts with a phenolic group on the haemoglobin molecule; or (vii) a reactive group from reaction with cyanogen bromide with the polysaccharide, which reacts with an amino group on the haeomoglobin molecule.

Any conventional activating groups may be used, but we prefer those activating groups disclosed in U.S. Pat. No. 4,064,118.

We particularly prefer the activating group to comprise an alkylating group and especially a bromoacetyl group.

A preferred activating group is haloacetylaminoalkylamino group, preferably a bromoacetylaminoalkylamino group and especially a bromoacetylaminoethylamino group.

The aforementioned activating groups may be blocked by reaction with an amino compound, e.g. tyrosine; or a sulphydryl.

The content of activating groups may be determined by hydrolysis, preferably basic hydrolysis, e.g. with NaOH, of the compound. For example, when the activating group contains bromine, hydrolysis with NaOH converts on a one-to-one basis the activating groups to bromide ions. The activating group content may be determined using conventional analytic techniques known per se, e.g. by ion cromatography, or when the activating group contains bromine, using a bromide electrode.

The P$_{50}$ value of the compounds of formula I may be determined from their oxygen dissociation curves as determined, for example, by the method of Benesch, MacDuff and Benesch (1965) Anal. Biochem 11 81–87.

The compounds of formula I may have a P$_{50}$ value at 24° C. of greater than 7 mm Hg, preferably greater than 8 mm Hg, more preferably greater than 9 mm Hg and most preferably greater than 10 mm Hg.

Bromoacetylaminoethylamino activating groups are preferably blocked by reaction with a suitable compound containing a sulphydryl group.

Suitable compounds containing a sulphydryl group are those which do not substantially affect the oxygen affinity of the product and include cysteine (2-amino-3-mercaptopropionic acid), cysteamine (2-aminomethyl mercaptan), 2-mercaptoethanol, 2-mercaptoethanesulphonic acid and preferably 3-mercaptopropionic acid.

High proportions of sulphydryl compound to haemoglobin may lead to damage of the haem group and are therefore preferably avoided. When the compound of formula II is at a concentration of 6–8% w/v with respect to haemoglobin, the concentration of sulphydryl compound used is preferably less than 160 mM, preferably less than 80 mM and more preferably less than 50 mM. We particularly prefer the sulphydryl compound concentration to be at a concentration of 15–20 mM, e.g. about 16 mM.

For an effective reaction and one which avoids damage to the haemoglobin the pH is preferably in the range 7 to 11.5, more preferably in the range 8.5 to 10.5 and most preferably in the range 9 to 10, e.g. about 9.5.

The reaction with a compound capable of deactivating activating groups is preferably carried out below about 25° C. and more preferably between 0° and 5° C.

After reaction with a compound capable of deactivating activating groups, the compound of formula I or III may be isolated by conventional methods known per se, e.g. by dialysis.

We prefer the polysaccharide to be of molecular weight of from about 5,000 to 20,000,000, e.g. to be of average molecular weight of from about 10,000 to 100,000. The polysaccharide may be, e.g. hydroxyethyl starch, but we particularly prefer the polysaccharide to be a dextran of average molecular weight 70,000, 40,000 or 20,000.

We prefer H to be an Hb-Z group. We also prefer Z to be a polyol, two or more of the hydroxy groups of which are esterified with phosphoric acid. We particularly prefer Z to contain from 2 to 6, and more preferably 2 to 4, phosphate groups. When Z is a phosphate ester of a polyol, at least 2, and preferably all, of the hydroxy groups have been esterified with phosphoric acid. We also prefer Z to contain from 4 to 8 carbon atoms and to be a straight chain group. We further prefer Z to comprise a polyol in which each of the carbon atoms (other than at least one of the terminal carbon atoms) carries an optionally phosphoric acid esterified hydroxy group.

The Z group may be linked to the haemoglobin according to the method disclosed in U.S. Pat. No. 4,650,786.

We prefer the Z group to be derived from an inositol phosphate. Inositol phosphates are known compounds and may be made and isolated in a manner which is also known per se. We particularly prefer the Z group to be derived from inositol tetraphosphate, e.g. from a mixture containing a major proportion of inositol tetraphosphate and a minor proportion of other inositol phosphates.

According to the invention we further provide a water soluble compound having a molecular weight of from about 70,000 to about 2,000,000 and having the formula III, $$(PS)_a-X-(Hb)-Z \qquad \text{III}$$

in which X, Hb and Z are as defined in claim 1, and $(PS)_a$ is a polysaccharide of molecular weight from about 2,000 to about 200,000 comprising less than 0.4 moles activating group per mole of haemoglobin.

The compounds of formula III may be prepared by blocking an activated compound of formula II using the method as hereinbefore described.

We prefer the number of moles of activating groups to moles of haemoglobin to be less than 0.2 and more preferably less than 0.1.

The haemoglobin content of the compound may be determined using conventional techniques known per se, e.g. by spectrophotometric analysis (measurement of optical density at a given wavelength e.g. 415 mm) or by the method of D. L. Drabkin and J. H. Austin, J. Biological Chemistry, Vol. 112, pp. 51–65 (1935).

The compounds of formula II may, for example, be prepared as described in Example 1 of European Patent No. 0,140,640.

The haemoglobin referred to in this specification may be derived from any appropriate animal, e.g. a bovine animal, but is preferably human haemoglobin.

INDUSTRIAL APPLICABILITY

The compounds of the invention are useful in that they have oxygen transporting capability. Thus the compounds are useful as immobilised oxygen extractants, for example, in the system described in U.S. Pat. No. 4,343,715. The compounds are also indicated for use in blood substitute or blood expander compositions. Thus the compounds may be used to provide enhanced oxygenation of poorly perfused tissues. Such poorly perfused tissues may be present in cancerous growths, in cases of myocardial infarction or in cases of cerebral haemorrhage. The compounds may also be used as blood substitutes, e.g. for the victims of accidents or violence; where blood typing and matching is not possible or is not possible in the time available; where patients are at risk from, or refuse, normal blood transfusion; for the purpose of delivery of oxygen to tissues or organs which are to be preserved; for priming extracorporeal circulatory systems; or for other situations where erythrocytes are normally indicated.

According to the invention, we provide a compound of formula I for use as a pharmaceutical. In particular, we provide a compound of formula I for use in the preparation of a pharmaceutical for the treatment of poorly oxygenated tissues.

The compounds may be administered to the patients concerned in admixture with a pharmaceutically acceptable excipient, diluent or carrier, for example as an aqueous solution, which may be a buffered balanced salt solution.

According to the invention, we provide a pharmaceutical formulation comprising a compound of formula I in admixture with a pharmaceutically acceptable adjuvant, diluent or carrier.

In general, the compounds will be administered using types of formulations, packages and forms of administration which are conventional for the administration of blood plasma expanders. The compounds may also be freeze dried, optionally with a cryoprotective agent, and subsequently be reconstituted for use.

The amount of the compound which is administered will vary with the size, condition of the patient and treatment desired. However, in certain severe instances substantially all the patient's blood may be replaced by a formulation containing a compound of the invention.

The compounds of the invention are advantageous in that they possess more desirable oxygen absorption and release properties and have a longer shelf life, e.g. increases in viscosity on storage are reduced, than similar known compounds. The compounds of the invention are also advantageous in that they may be prepared easily and in relatively high yield.

The compounds of the invention are capable of being administered to mammals in order to replace the hosts haemoglobin. We further provide a compound according to the invention for use as a pharmaceutical for the replacement of up to 99% v/v haemoglobin, preferably up to 98% v/v, more preferably up to 96% v/v and especially up to 95% v/v.

The invention is illustrated, but in no way limited, by the following Examples in which temperatures are in degrees centigrade and viscosities were measured using an Ostwald viscometer at 37° C.

EXAMPLE 1

Preparation of a compound of formula I (a) Formation of a compound of formula II The following procedure was carried out at 0°–4°. N-bromoacetylaminoethylamino-dextran-haemoglobin (Br-dxHb) was made by an overnight incubation of N-bromoacetylamino ethylamino-dextran (Br-dx) (prepared according to the method of Example 1 of U.S. Pat. No. 4,064,118) and haemoglobin (Hb) in 0.05M sodium bicarbonate. 100 ml of ice cold 6% w/v (with respect to Hb) Br-dxHb in 0.05M sodium bicarbonate (pH=9.5) was combined with 4.45 ml of 2M bis [2-hydroxyethyl]-imino-tris-[hydroxymethyl]methane (bis-Tris) (pH 7.5). To this mixture 0.5 g inositol tetrakisphosphate dialdehyde (FPA) in 68 ml 0.05M sodium acetate (pH=5.2) was added. The pH was adjusted to 7.4 using 0.1N NaOH, 10 ml of 0.5M dimethyl amine borane was added and the mixture incubated for 2 hours at 0° with stirring. An 8% w/v aqueous solution was prepared.

(b) Treatment with 3-mercaptopropionic acid

Sodium bicarbonate was then added to the product of step (a) above, to a final concentration of 0.2M and the pH adjusted to 9.5 using 0.1N NaOH. 3-Mercaptopropionic acid was added to a final concentration of 16 mM. The mixture was then dialysed against 0.1M tris[hydroxymethyl]aminomethane hydrochloride (Tris-cl) buffer (pH 8.5) containing 1M NaCl and then against kidney dialysis-buffer (pH 7.4). An 8% w/v aqueous solution was prepared.

The bromoacetylaminoethylamino (BAEA) group content of the products of Examples 1(a) and 1(b) were measured according to the method of Example 4.

The viscosities of the solutions prepared according to Examples 1(a) and 1(b) were measured at intervals. The results are listed in Table I.

EXAMPLE 2

The procedure of Example 1(b) above was carried out using;

(a) L-cysteine
(b) mercaptoethanol in place of 3-mercaptopropionic acid. 8% w/v aqueous solutions of the products were prepared.

The BAEA group content of the products was measured according to the method of Example 4.

The viscosities of the solutions were measured at intervals. The results are listed in Table I.

EXAMPLE 3

(a) A 6% w/v aqueous solution of the product of Example 1(a) was prepared.
(b) A 6% w/v aqueous solution of the product of Example 1(b) was prepared.

The viscosities of the solutions were measured at intervals. The results are listed in Table I.

EXAMPLE 4

BAEA group content

The BAEA group content of the blood substitutes prepared as described in Examples 1 and 2(a) and (b) above was measured by the following method.

The product of Examples 1 and 2(a) and (b) were incubated in 0.1N NaOH for 30 minutes at 100°. The mixtures were then chilled on ice, neutralized to pH 7.0 (using 1N acetic acid), filtered and analysed for bromide content using ion chromatography.

EXAMPLE 5

The oxygen dissociation curves of the products of Examples 1 and 2(a) and (b) were determined using the method of Benesch, MacDuff and Benesch (1965) Anal. Biochem 11 81–87 (but using a temperature of 24° and 0.05M bis-Tris (pH 7.4)). The results are shown in FIG. 1 in which:

the x axis is Log $PO_2$ (partial pressure of $O_2$),
the y axis is % oxygenation,
(1) Compound of Example 1(a)
(2) Compound of Example 1(b)
(3) Compound of Example 2(b)
(4) Compound of Example 2(a)

The following $P_{50}$ values at 24° were determined from FIG. 1:
(1) 10.3 mm Hg
(2) 10.3 mm Hg
(3) 8.7 mm Hg
(4) 9.5 mm Hg.

TABLE I

| FPA-DxHb Preparation | Excess bromo group Content (mg/l) | BrAc:Hb* | Days stored at 4° | | | | | | |
|---|---|---|---|---|---|---|---|---|---|
| | | | 0 | 3 | 8 | 12 | 17 | 25 | 41 |
| | | | Viscosity | | | | | | |
| Example (a) | 400 | 400 | 7.765 | 9.510 | — | 22.78 | — | ** | |
| Example (1b) | 8 | 8.00 | 3.172 | 2.987 | — | 3.197 | — | 3.234 | 3.292 |
| Example (2b) | 3 | 3.00 | 3.575 | — | — | 3.804 | — | 4.134 | — |
| Example (2a) | 5 | 4.50 | 3.081 | — | — | 3.248 | — | 3.243 | — |
| Eaxmple (3a) | 300 | 400 | 2.213 | 2.232 | 2.626 | — | 3.099 | 3.548 | 7.134 |
| Example (3b) | 6 | 8.0 | 1.948 | 1.960 | 1.951 | — | 1.945 | 1.963 | 1.934 |

**Too viscous for measurement
*Bromoacetyl:haemoglobin ratio

We claim:

1. A water soluble compound having a molecular weight of from about 70,000 to about 2,000,000 and having the formula I,

B—X—(PS)—X—(H)    I in which PS is a polysaccharide of molecular weight from about 2,000 to about 2,000,000,
X is a covalently bonded chemical bridging group,
H is a group Hb or Hb-Z,
B is an activating group blocked by a sulphydryl group,
Hb is a haemoglobin residue, and
Z is an oxygen affinity reducing ligand containing two or more phosphate groups.

2. A compound according to claim 1 wherein the sulphydryl group is 3-mercaptopropionic acid.

3. A pharmaceutical formulation comprising a compound according to claim 1 in admixture with a pharmaceutically acceptable adjuvant, diluent or carrier.

4. A process for the production of a compound of formula I, which comprises
reaction of a compound of formula II,

A—X—(PS)—X—(H)    II in which X, H and PS are as defined in claim 1, and
A is an activating group,
with a compound capable of blocking an activating group.

5. A process according to claim 4 in which the compound capable of blocking the activating group contains a sulphydryl group.

* * * * *